US010175332B2

United States Patent
Keupp

(10) Patent No.: US 10,175,332 B2
(45) Date of Patent: Jan. 8, 2019

(54) MOTION TRIGGERED MR IMAGING USING APT/CEST

(75) Inventor: Jochen Keupp, Rosengarten (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1039 days.

(21) Appl. No.: 14/009,551

(22) PCT Filed: Apr. 2, 2012

(86) PCT No.: PCT/IB2012/051598
§ 371 (c)(1),
(2), (4) Date: Oct. 3, 2013

(87) PCT Pub. No.: WO2012/143808
PCT Pub. Date: Oct. 26, 2012

(65) Prior Publication Data
US 2014/0039297 A1 Feb. 6, 2014

(30) Foreign Application Priority Data
Apr. 19, 2011 (EP) .................................... 11163003

(51) Int. Cl.
*G01R 33/567* (2006.01)
*A61B 5/055* (2006.01)
*G01R 33/56* (2006.01)

(52) U.S. Cl.
CPC .......... *G01R 33/5673* (2013.01); *A61B 5/055* (2013.01); *G01R 33/5605* (2013.01); *G01R 33/567* (2013.01)

(58) Field of Classification Search
CPC ................................ G01R 33/20; A61B 5/055

USPC .......................................................... 600/413
See application file for complete search history.

(56) References Cited

U.S. PATENT DOCUMENTS

| | | | | |
|---|---|---|---|---|
| 6,958,604 B2* | 10/2005 | An | ........................ | G01V 3/32 324/300 |
| 6,963,769 B1* | 11/2005 | Balaban | ................ | A61B 5/055 324/307 |
| 7,684,847 B2* | 3/2010 | Itagaki | ............... | G01R 33/5601 324/306 |
| 8,126,532 B2 | 2/2012 | Miyoshi | | |
| 8,457,711 B2* | 6/2013 | Nezafat | ............. | G01R 33/5635 600/407 |
| 8,536,866 B2* | 9/2013 | Van Zijl | ............... | G01R 33/483 324/307 |
| 8,686,727 B2* | 4/2014 | Reddy | ............... | G01R 33/5601 324/307 |
| 9,121,917 B2* | 9/2015 | Song | .................. | G01R 33/5601 |

(Continued)

FOREIGN PATENT DOCUMENTS

JP 2008142479 A 6/2008
WO 2010058732 A1 5/2010

*Primary Examiner* — Angela M Hoffa

(57) ABSTRACT

A method of MR imaging a moving portion of a body includes detecting a motion signal from the body while continuously subjecting the moving portion of the body to one or more preparation RF pulses; subjecting the moving portion of the body to an imaging sequence including an excitation RF pulse and switched magnetic field gradients, wherein the imaging sequence is triggered by the detected motion signal; acquiring MR signals from the moving portion of the body; and reconstructing an MR image from the acquired MR signals.

12 Claims, 2 Drawing Sheets

(56) References Cited

U.S. PATENT DOCUMENTS

| | | | |
|---|---|---|---|
| 2005/0165295 A1* | 7/2005 | Li | G01R 33/56 600/410 |
| 2007/0038069 A1* | 2/2007 | Itagaki | G01R 33/5601 600/410 |
| 2007/0069726 A1* | 3/2007 | Miyoshi | G01R 33/5614 324/307 |
| 2008/0150532 A1* | 6/2008 | Slavin | G01R 33/50 324/318 |
| 2011/0288402 A1* | 11/2011 | Pikkemaat | G01R 33/5616 600/420 |
| 2013/0190601 A1* | 7/2013 | Alsop | G01R 33/5601 600/410 |
| 2013/0342207 A1* | 12/2013 | Keupp | G01R 33/3614 324/309 |
| 2014/0117987 A1* | 5/2014 | Yui | G01R 33/28 324/309 |
| 2014/0213887 A1* | 7/2014 | Reddy | G01R 33/5605 600/414 |
| 2015/0051474 A1* | 2/2015 | Eggers | G01R 33/5605 600/410 |

\* cited by examiner

MOTION TRIGGERED MR IMAGING USING APT/CEST

CROSS-REFERENCE TO PRIOR APPLICATIONS

This application is the U.S. National Phase application under 35 U.S.C. § 371 of International Application No. PCT/IB2012/051598, filed on Apr. 2, 2012, which claims the benefit of European Patent Application No. 11163003.4, filed on Apr. 19, 2011. These applications are hereby incorporated by reference herein.

TECHNICAL FIELD

The invention relates to the field of magnetic resonance (MR) imaging. It concerns a method of MR imaging of a moving portion of a body. The invention also relates to a MR device and to a computer program for a MR device.

Image-forming MR methods which utilize the interaction between magnetic fields and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

BACKGROUND OF THE INVENTION

According to the MR method in general, the body of the patient to be examined is arranged in a strong, uniform magnetic field whose direction at the same time defines an axis (normally the z-axis) of the co-ordinate system on which the measurement is based. The magnetic field produces different energy levels for the individual nuclear spins in dependence on the magnetic field strength which can be excited (spin resonance) by application of an electromagnetic alternating field (RF field) of defined frequency (so-called Larmor frequency, or MR frequency). From a macroscopic point of view, the distribution of the individual nuclear spins produces an overall magnetization which can be deflected out of the state of equilibrium by application of an electromagnetic pulse of appropriate frequency (RF pulse) while the magnetic field of the RF pulse extends perpendicular to the z-axis, so that the magnetization performs a precession about the z-axis. This motion of the magnetization describes a surface of a cone whose angle of aperture is referred to as flip angle. The magnitude of the flip angle is dependent on the strength and the duration of the applied electromagnetic pulse. In the case of a so-called 90° pulse, the spins are deflected from the z axis to the transverse plane (flip angle 90°). The RF pulse is radiated toward the body of the patient via a RF coil arrangement of the MR device. The RF coil arrangement typically surrounds the examination volume in which the body of the patient is placed.

After termination of the RF pulse, the magnetization relaxes back to the original state of equilibrium, in which the magnetization in the z direction is built up again with a first time constant $T_1$ (spin lattice or longitudinal relaxation time), and the magnetization in the direction perpendicular to the z direction relaxes with a second time constant $T_2$ (spin-spin or transverse relaxation time). The variation of the magnetization can be detected by means of receiving RF coils which are arranged and oriented within the examination volume of the MR device in such a manner that the variation of the magnetization is measured in the direction perpendicular to the z-axis. The decay of the transverse magnetization is accompanied, after application of, for example, a 90° pulse, by a transition of the nuclear spins (induced by local magnetic field inhomogeneities) from an ordered state with the same phase to a state in which all phase angles are uniformly distributed (dephasing). The dephasing can be compensated by means of a refocusing pulse (for example a 180° pulse). This produces an echo signal (spin echo) in the receiving coils.

In order to realize spatial resolution in the body, linear magnetic field gradients extending along the three main axes are superposed on the uniform magnetic field, leading to a linear spatial dependency of the spin resonance frequency. The signal picked up in the receiving coils then contains components of different frequencies which can be associated with different locations in the body. The signal data obtained via the receiving coils corresponds to the spatial frequency domain and is called k-space data. The k-space data usually includes multiple lines acquired with different phase encoding. Each line is digitized by collecting a number of samples. A set of k-space data is converted to a MR image by means of Fourier transformation.

In some medical applications, the difference in MR signal intensity from standard MR protocols, i.e. the contrast, between different tissues might not be sufficient to obtain satisfactory clinical information. In this case, contrast enhancing techniques are applied, which rely for example on advanced MR sequences or on MR contrast agents, like paramagnetic agents (Gd-DTPA/DOTA), or combinations of both.

In a number of important MR applications with or without using contrast agents, advanced contrast enhancing MR techniques are favorable, which employ long and/or repeatedly applied preparation RF pulses, for example for saturation transfer, hetero- or homonuclear polarization transfer, proton decoupling or spin locking.

A particularly promising approach for contrast enhancement and increase of MR detection sensitivity (by orders of magnitude) is the known method based on 'Chemical Exchange Saturation Transfer' (CEST), as initially described by Balaban et al. (see e.g. U.S. Pat. No. 6,962,769 B1). With this CEST technique, the image contrast is obtained by altering the intensity of the water proton signal in the presence of a contrast agent with a fast-relaxing proton pool resonating at a slightly different frequency than the main water resonance. This is achieved by selectively saturating the nuclear magnetization of the pool of exchangeable protons which resonate at a frequency different from the water proton resonance. Exchangeable protons can be provided by exogenous CEST contrast agents (e.g. DIACEST, PARACEST or LIPOCEST agents), but can also be found in biological tissue (e.g. endogenous amide protons in proteins and peptides or protons in glucose, not covered in the original Balaban method). A frequency-selective preparation RF pulse that is matched to the MR frequency of the exchangeable protons is used for this purpose. The saturation of the MR signal of the exchangeable protons is subsequently transferred to the MR signal of nearby water protons within the body of the examined patient by chemical exchange or dipolar coupling with the water protons, thereby decreasing the water proton MR signal. The selective saturation at the MR frequency of the exchangeable protons thus gives rise to a negative contrast in a proton-density weighted MR image. Amide proton transfer (APT) MR imaging of endogenous exchangeable protons allows highly sensitive and specific detection of pathological processes on a molecular level, like increased protein concentrations in malignant tumor tissue. The APT signal is also sensitively reporting on locally altered pH levels—because the exchange rate is pH dependent—which can be e.g. used to characterize ischemic stroke. CEST contrast agents have several important advantages over $T_1$- and $T_2$-based MR contrast agents. CEST contrast agents allow for multiplexing by using a single compound or a mixture of compounds bearing exchangeable protons that can be addressed separately in a multi-frequency CEST MR examination. This is of particular interest for molecular imaging, where multiple biomarkers may be associated with several unique CEST frequencies. Moreover, the MR contrast in APT/CEST MR imaging can be turned on and off at will by means of the frequency selective preparation RF pulse. Adjustable contrast enhancement is highly advantageous in many applications, for example when the selective uptake of the contrast agent in the diseased tissue in examined body is slow.

A problem of all known APT/CEST MR imaging techniques is that the selective saturation prior to the actual acquisition of image data takes a comparably long time. The build-up of the saturation of the exchangeable protons is a relatively slow process (the characteristic timescale is on the order of one second). Consequently, the desirable saturation period for APT/CEST measurements is typically 2-5 seconds. Then, immediately following the saturation period, an imaging sequence including a (slice-selective) excitation RF pulse is usually applied for excitation of bulk water nuclear magnetization and one or more MR signals are recorded, for example as gradient echoes or spin echoes. The acquisition of individual MR signals used for imaging takes typically several milliseconds up to a few hundred milliseconds, wherein the full k-space is acquired as a set of these short signal acquisitions.

Further, in the paper '*Magnetisation transfer contrast in MR imaging of the heart*' by R. S. Balaban et al. in Radiology 180(1991)671-675 a gated acquisition of magnetic resonance signals is mentioned for MTF transfer. Off-resonance irradiation is applied during interpulse delay.

In clinical applications for MR examination of body regions affected by motion (for example abdominal organs like liver, prostate, and kidneys), APT/CEST MR imaging should be combined with motion detection to acquire MR signals in a defined motion state. For example, MR imaging of abdominal organs is affected by respiratory motion. Hence, APT/CEST MR imaging should be combined with breathing triggering to acquire the MR signals in a defined respiratory phase (e.g. full expiration). Triggering the imaging sequence for MR signals acquisition by detected motion signals is per se known in the art. However, a conventional motion triggering, in which the imaging sequence is initiated upon the respective trigger signal, would be inappropriate and inefficient for APT/CEST MR imaging. The motion phase will have changed until the MR signal acquisition starts several seconds later, because, for example the human breathing interval, which amounts to 3-5 seconds, covers a time scale which is similar to the duration of the selective saturation prior to the actual MR signal acquisition. Furthermore, in the described example, waiting for the trigger signal indicating the desired respiratory phase will take up to one complete breathing cycle, which compromises scan efficiency.

Until today, no efficient combination of APT/CEST MR imaging with motion triggering has been described in the art.

From the foregoing it is readily appreciated that there is a need for an improved MR imaging technique. It is consequently an object of the invention to provide a MR imaging method and a MR device which enable high-quality MR imaging of moving body portions using APT/CEST.

SUMMARY OF THE INVENTION

In accordance with the invention, a method of MR imaging of a moving portion of a body is disclosed. The method comprises the steps of:

detecting a motion signal from the body while continuously subjecting the portion of the body to one or more preparation RF pulses;

subjecting the portion of the body to an imaging sequence comprising at least one excitation RF pulse and switched magnetic field gradients, wherein the imaging sequence is triggered by the detected motion signal;

acquiring MR signals from the portion of the body; and reconstructing a MR image from the acquired MR signals.

The invention proposes to apply the preparation RF pulses continuously during any motion phase of the examined portion of the body, while MR signal acquisition is performed only in one pre-defined motion state (e.g. full expiration). The imaging sequence is triggered at an instant at which the given motion state is recognized on the basis of the detected motion signals. The motion signals represent the motion phase of the movement of the examined portion of the body. The method of the invention enables motion-triggered APT/CEST MR imaging of, for example, the abdomen. The method of the invention is characterized by superior scan time efficiency and robustness since the preparation RF pulses are radiated continuously. That is, the preparation RFpulses are repeatedly applied in a continuous series while movement of the examined portion occurs. The actual MR signal acquisition can start immediately after recognition of the desired motion state on the basis of the detected motion signals. Alternatively, the actual MR signal acquisition can be triggered after a pre-determined time delay, so that a prospective initialisaton of the MR signal acquisition is applied. The pre-determined time delay can be set on the basis of the type of repetitive motion at hand, such as respiratory motion or cardiac motion. The method of the invention provides accurate motion compensation. High-quality MR imaging without motion artifacts can thus be obtained.

According to a preferred embodiment of the invention, the motion signals are detected via a motion sensor. Motion sensors, which are well-suited for application according to the invention, are per se known in the art. For example WO 2006/099011 A1 discloses a wireless in-bore patient monitor for MR imaging which enables detection of the respiratory phase during MR signal acquisition.

In a possible embodiment of the invention, the continuously applied preparation RF pulses are extended over multiple cycles of the motion signal. Thus, the MR data acquisition is only performed at every second, every third (every N-th) occurrence of the pre-defined motion state. This is advantageous in cases, in which the preparation is required for a period, which is longer than the typical duration of a single motion cycle (e.g. cardiac or breathing cycle).

The approach of the invention can advantageously be used in combination with different types of preparation RF pulses. The preparation RF pulses of the method of the invention may be, for example, saturation RF pulses for saturating nuclear magnetization, or spin locking RF pulses for measuring $T_{1\rho}$, or homo-nuclear or hetero-nuclear polarization transfer RF pulses for transferring magnetization between different nuclear spins for nuclear Overhauser enhanced (NOE) MR imaging, or proton decoupling RF pulses in multi-nuclear MR imaging. In particular, the preparation RF pulses of the method of the invention can be frequency-selective saturation RF pulses for saturating nuclear magnetization of protons of an exchangeable pool, belonging to endogenous molecules or to a CEST contrast agent.

APT/CEST MR imaging is particularly constrained by the safety regulations for heat deposition (SAR) in the tissue of the examined patient because the long and powerful RF irradiation during saturation results in a considerable SAR contribution. According to a preferred embodiment of the invention, the number and/or the duration of the continuously radiated preparation RF pulses are monitored, the radiation of the preparation RF pulses being interrupted as soon as the monitored number and/or the duration between two consecutive imaging sequences exceeds a pre-defined limit. This embodiment of the invention ensures a SAR-safe operation. The pre-defined limit determines a time interval during which the preparation RF pulses are repeatedly radiated. If the actual motion interval, as recognized on the basis of the motion signals, exceeds the limit, the preparation RF pulses are switched off automatically. Optionally, the operator of the used MR device can be informed.

The method of the invention described thus far can be carried out by means of a MR device including at least one main magnet coil for generating a uniform steady magnetic field within an examination volume, a number of gradient coils for generating switched magnetic field gradients in different spatial directions within the examination volume, at least one RF coil for generating RF pulses within the examination volume and/or for receiving MR signals from a body of a patient positioned in the examination volume, a motion sensor which is sensitive to motion of a moving portion of the body, a control unit for controlling the temporal succession of RF pulses and switched magnetic field gradients, and a reconstruction unit for reconstruction of a MR image from the received MR signals. The method of the invention is preferably implemented by a corresponding programming of the control unit of the MR device.

The methods of the invention can be advantageously carried out in most MR devices in clinical use at present. To this end it is merely necessary to utilize a computer program by which the MR device is controlled such that it performs the above-explained method steps of the invention. The computer program may be present either on a data carrier or be present in a data network so as to be downloaded for installation in the control unit of the MR device.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF THE EMBODIMENTS

Figure 1:
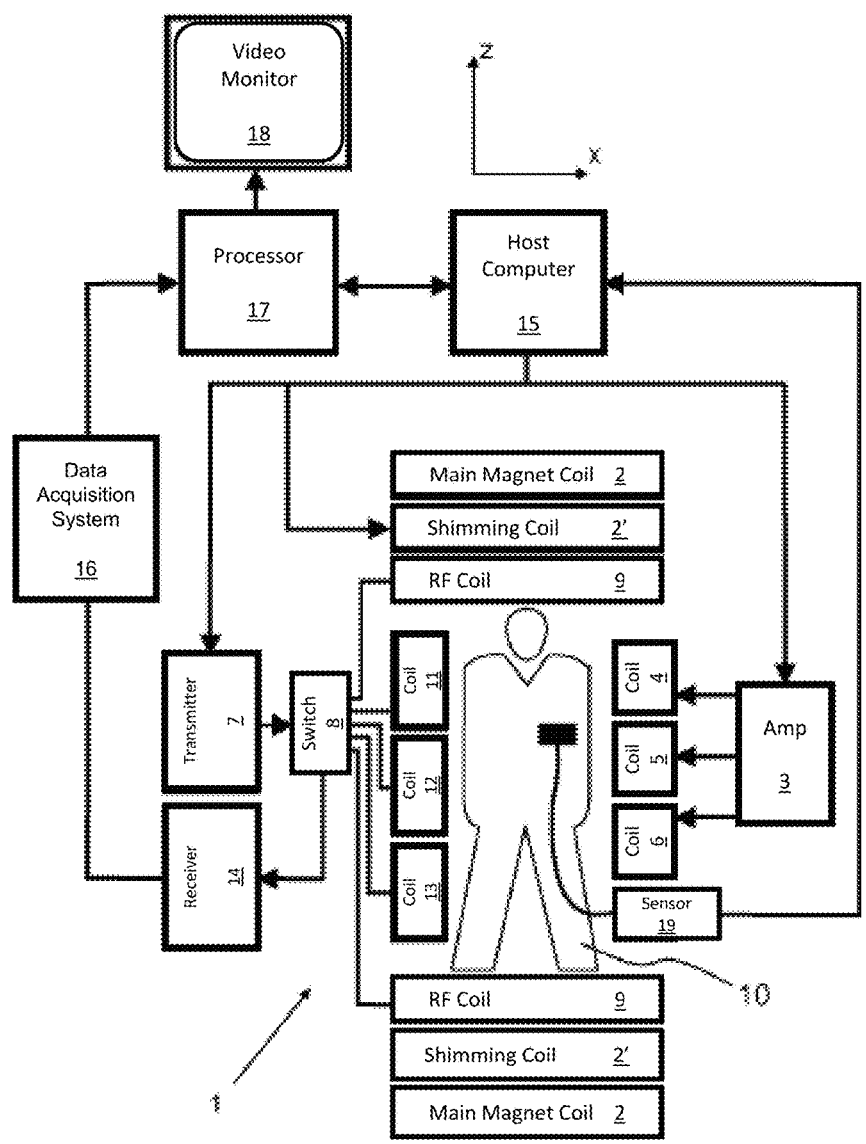
FIG. 1 shows a MR device according to the invention.

With reference to FIG. 1, a MR device 1 is shown. The device comprises superconducting or resistive main magnet coils 2 such that a substantially uniform, temporally constant main magnetic field $B_0$ is created along a z-axis through an examination volume. The device further comprises a set of ($1^{st}$, $2^{nd}$, and—where applicable—$3^{rd}$ order) shimming coils 2', wherein the current flow through the individual shimming coils of the set 2' is controllable for the purpose of minimizing $B_0$ deviations within the examination volume.

A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

Most specifically, a gradient pulse amplifier 3 applies current pulses to selected ones of whole-body gradient coils 4, 5 and 6 along x, y and z-axes of the examination volume. A digital RF frequency transmitter 7 transmits RF pulses or pulse packets, via a send-/receive switch 8, to a body RF coil 9 to transmit RF pulses into the examination volume. A typical MR imaging sequence is composed of a packet of RF pulse segments of short duration which jointly achieve a selected manipulation of nuclear magnetic resonance in combination with any applied magnetic field gradients. The RF pulses are used to saturate, excite resonance, invert magnetization, refocus resonance, or manipulate resonance and select a portion of a body 10 positioned in the examination volume. The MR signals are also picked up by the body RF coil 9 or/and multiple local RF receiver array coils 11, 12, 13.

For generation of MR images of limited regions of the body 10 by means of parallel imaging, a set of local array RF coils 11, 12, 13 are placed contiguous to the region selected for imaging. The array coils 11, 12, 13 can be used to receive MR signals induced by body-coil RF transmissions.

The resultant MR signals are picked up by the body RF coil 9 and/or by the array RF coils 11, 12, 13 and demodulated by a receiver 14 preferably including a preamplifier (not shown). The receiver device 14 is connected to the RF coils 9, 11, 12 and 13 via the send-/receive switch 8.

A host computer 15 controls the current flow through the shimming coils 2' as well as the gradient pulse amplifier 3 and the transmitter 7 to generate any of a plurality of MR imaging sequences, such as echo planar imaging (EPI), gradient and spin echo imaging, fast spin echo imaging, and the like. For the selected sequence, the receiver 14 receives a single or a plurality of MR data lines from all active receiving RF coils in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies a Fourier transform or other appropriate reconstruction algorithms, such like SENSE or GRAPPA or the like. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

The depicted MR device 1 further comprises a motion sensor 19 connected to a sensor element which is located on the patient's body 10 within the examination volume. The motion sensor 19 detects motion signals which indicate, in the depicted embodiment, the momentary respiratory phase of the patient.

Figure 2:
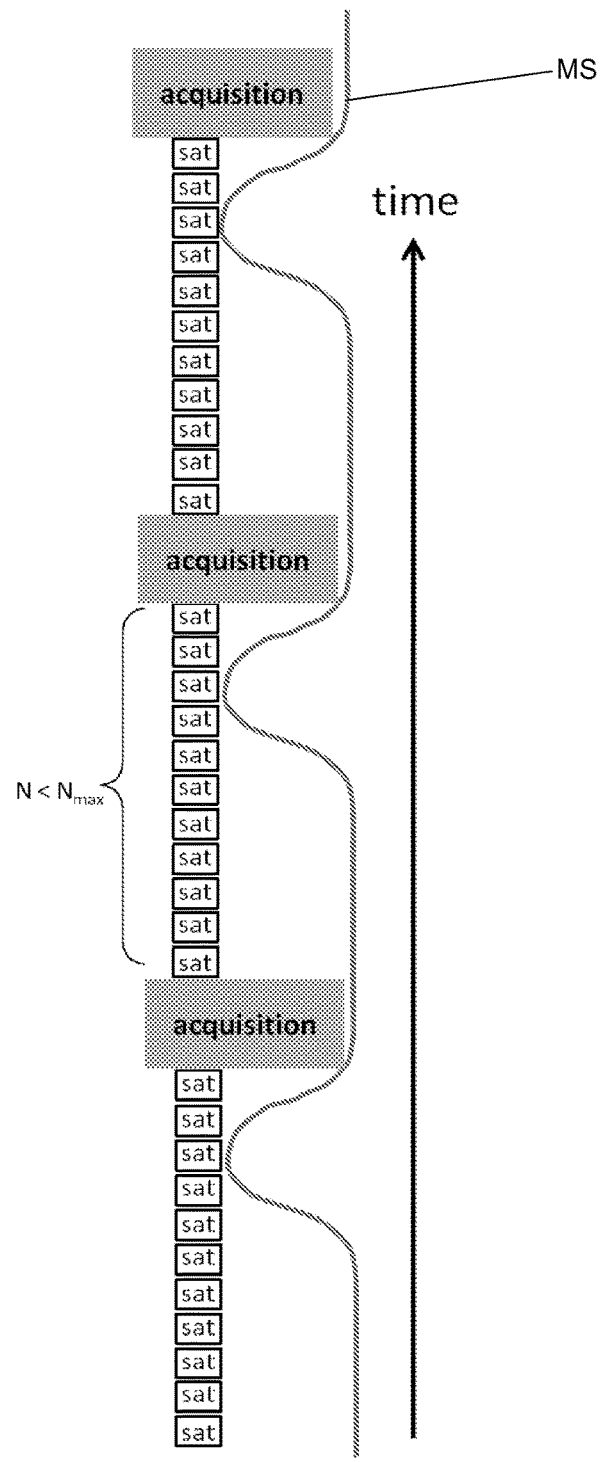
FIG. 2 shows a timing diagram illustrating the method steps of the invention.

With continuing reference to FIG. 1 and further reference to FIG. 2, the method of the invention is illustrated. FIG. 2 shows a timing diagram with the different method steps of the invention.

In the depicted embodiment, respiratory motion signals are acquired from the body 10 via the motion sensor 19. The motion signal is designated by MS in FIG. 2.

The motion signal MS is detected from the body 10 while the imaged body portion is continuously subjected to repeatedly radiated saturation RF pulses for saturating nuclear magnetization of an exchangeable proton pool according to the APT/CEST technique. As soon as a motion state of full expiration is recognized on the basis of the motion signal MS, an imaging sequence comprising at least one excitation RF pulse is triggered and MR signals generated by the imaging sequence are acquired during a pre-determined acquisition interval. The preparation RF pulses applied between the successive MR signal acquisition steps are designated by "sat" in FIG. 2. The acquisition intervals are designated by "acquisition".

The number N of the repeatedly radiated preparation RF pulses is monitored in the time interval between successive MR signal acquisition steps. The radiation of the preparation RF pulses is interrupted automatically as soon as the monitored number N exceeds a pre-defined limit $N_{max}$. In this way a safe operation regarding RF heat deposition (SAR) is ensured.

The above described MR imaging method of the invention enables motion-triggered APT/CEST applications, for example for APT/CEST MR imaging of the abdomen. The method of the invention is characterized by superior scan time efficiency and robustness due to the preparation RF pulses being radiated continuously during the time interval during which the next triggering event is waited for. Accurate motion compensation is achieved by pre-defining a motion state, in which MR signals are acquired. SAR-safe operation is ensured by avoiding that the number or duration of preparation RF pulses exceeds a pre-determined limit.

The invention claimed is:

1. A method of magnetic resonance (MR) imaging a moving portion of a body, the method comprising:
   detecting a motion signal from the body while continuously subjecting the portion of the body to one or more preparation radio-frequency (RF) pulses;
   detecting a desired respiratory motion state of the moving portion of the body from the detected motion signal;
   subjecting the moving portion of the body to an imaging sequence comprising an excitation RF pulse and switched magnetic field gradients, wherein the imaging sequence is triggered by the detection of the desired respiratory motion state;
   acquiring MR signals from the moving portion of the body, wherein the MR signals are affected by one or more of the preparation RF pulses and the imaging sequence, and
   reconstructing an MR image from the acquired MR signals, wherein
   the radiation of the one or more preparation RF pulses is interrupted when the duration between two consecutive imaging sequences exceeds a pre-defined limit.

2. The method of claim 1, wherein the desired respiratory motion state is a pre-defined motion state.

3. The method of claim 1, wherein the motion signal is detected via a motion sensor.

4. The method of claim 1, wherein the preparation RF pulses are:
   saturation RF pulses for saturating nuclear magnetization,
   spin locking RF pulses,
   polarization transfer RF pulses for transferring magnetization between different nuclear spins, or
   proton decoupling RF pulses.

5. The method of claim 4, wherein the preparation RF pulses are frequency-selective saturation RF pulses for saturating nuclear magnetization of protons of an exchangeable endogenous proton pool or of a chemical-exchange saturation transfer (CEST) contrast agent.

6. The method of claim 1, wherein:
   the number (N) of the repeatedly radiated preparation RF pulses are monitored, and
   the radiation of the preparation RF pulses is interrupted as soon as the monitored number (N) of the repeatedly radiated preparation RF pulses exceeds a pre-defined limit ($N_{max}$).

7. The method of claim 1, wherein the preparation RF pulses are spin locking RF pulses.

8. The method of claim 1, wherein the preparation RF pulses are polarization transfer RF pulses for transferring magnetization between different nuclear spins.

9. The method of claim 1, wherein the preparation RF pulses are proton decoupling RF pulses.

10. The method of claim 1, wherein the acquiring of the MR data is performed at every $N^{th}$ occurrence of detecting the desired respiratory motion state of the moving portion of the body for a period of time.

11. A magnetic resonance (MR) device comprising:
    a main magnet coil for generating a uniform, steady magnetic field within an examination volume;
    gradient coils for generating switched magnetic field gradients in different spatial directions within the examination volume;
    a radio-frequency (RF) coil for generating an excitation RF pulse within the examination volume and/or for receiving MR signals from the body of a patient positioned in the examination volume;
    a motion sensor which is sensitive to motion of a moving portion of the body;
    a controller configured to control the temporal succession of the excitation RF pulse and the switched magnetic field gradients; and
    a processor configured to reconstruct an MR image from the received MR signals, wherein:
    the controller is further configured to perform the operations of:
       detecting a motion signal from the body via the motion sensor while continuously subjecting the moving portion of the body to one or more preparation RF pulses;
       subjecting the moving portion of the body to an imaging sequence comprising the excitation RF pulse and the switched magnetic field gradients, wherein the imaging sequence is triggered by the detection of the motion signal; and
       interrupting the radiation of the one or more preparation RF pulses when the duration between two consecutive imaging sequences exceeds a pre-defined limit, and
    the processor is further configured to perform the operations of:
       acquiring MR signals from the moving portion of the body; and reconstructing an MR image from the acquired MR signals.

12. A non-transitory computer-readable medium comprising instructions that, when executed by a computer processor, execute a method of magnetic resonance (MR) imaging a moving portion of a body, the method comprising:
- detecting a motion signal from the body while continuously subjecting the moving portion of the body to one or more preparation radio-frequency (RF) pulses;
- detecting a desired respiratory motion state of the moving portion of the body from the detected motion signal;
- subjecting the moving portion of the body to an imaging sequence comprising an excitation RF pulse and switched magnetic field gradients, wherein the imaging sequence is triggered by the detection of the desired respiratory motion state;
- acquiring MR signals from the moving portion of the body, wherein the MR signals are affected by one or more of the preparation RF pulses and the imaging sequence, and
- reconstructing an MR image from the acquired MR signals, wherein
- the radiation of the one or more preparation RF pulses is interrupted when the duration between two consecutive imaging sequences exceeds a pre-defined limit.

* * * * *